United States Patent [19]

Hayes et al.

[11] Patent Number: 4,518,598

[45] Date of Patent: May 21, 1985

[54] 1,2,4-TRIAZOLE-3-AMINES, THEIR PHARMACEUTICAL COMPOSITIONS AND METHOD OF USE

[75] Inventors: Roger Hayes; David E. Bays; John W. M. Mackinnon; Linda Carey; Philip Blatcher, all of Hertfordshire, England

[73] Assignee: Glaxo Group Limited, London, England

[21] Appl. No.: 569,151

[22] Filed: Jan. 9, 1984

Related U.S. Application Data

[63] Continuation of Ser. No. 401,397, Jul. 23, 1982, abandoned.

[30] Foreign Application Priority Data

Feb. 23, 1982 [GB] United Kingdom ................ 8205596

[51] Int. Cl.³ .................... A61K 31/41; C07D 249/14
[52] U.S. Cl. .................................. 514/212; 546/210; 546/276; 548/193; 548/214; 548/266; 548/267; 544/132; 514/228; 514/229; 514/232; 514/236; 514/237; 514/316; 514/318; 514/326; 514/333; 514/340; 514/364; 514/383
[58] Field of Search ................ 544/132; 546/210, 276; 548/266, 267, 214, 193; 424/270, 248.56, 267, 269, 263

[56] References Cited

U.S. PATENT DOCUMENTS 4,450,168  5/1984  Bays et al. .......................... 546/210

FOREIGN PATENT DOCUMENTS 2063253  6/1981  United Kingdom ................ 548/266
2075007  11/1981  United Kingdom ................ 548/266

Primary Examiner—Robert T. Bond
Attorney, Agent, or Firm—Bacon & Thomas

[57] ABSTRACT

The invention relates to compounds of the general formula (I)

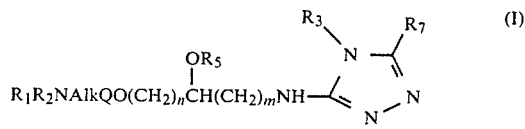

and physiologically acceptable salts, and hydrates thereof. The substituents are defined in the specification.

The compounds show pharmacological activity as selective histamine $H_2$-antagonists.

6 Claims, No Drawings

1,2,4-TRIAZOLE-3-AMINES, THEIR PHARMACEUTICAL COMPOSITIONS AND METHOD OF USE

This application is a continuation of application Ser. No. 401,397, filed July 23, 1982, now abandoned.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and schild, Brit. J. Pharmacol. Chemother, 1966, 27, 427). Their ability to do so can be demonstrated in the perfused rat stomach using the method described in British Patent Specification Number 1,665,960, modified by the use of sodium pentobarbitone (50 mg/kg, as anaesthetic instead of urethane, and in conscious dogs equipped with Heidenhain pouches using the method described by Black et al, Nature 1972 236, 385. Furthermore, the compounds antagonise the effect of histamine on the contraction frequency of isolated guinea pig right atrium.

Compounds with histamine $H_2$-blocking activity may be used in the treatment or conditions where there is an advantage in lowering gastric acidity, particularly in gastric and peptic ulceration, as a prophylactic measure in surgical procedures, and in the treatment of allergic and inflammatory condition where histamine is a known mediator. Thus they may be used for example, either alone or in combination with other active ingredients in the treatment of allergic and inflammatory conditions of the skin.

The present invention provides compounds of the general formula (I).

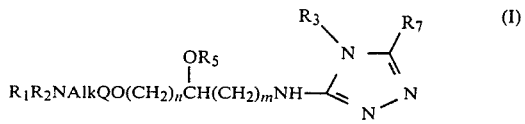

and physiologically acceptable salts, hydrates and bioprecursors thereof, in which $R_1$ represents hydrogen, $C_{1-14}$ alkyl, cycloalkyl, alkenyl, alkynyl, aralkyl, trifluoroalkyl, heteroaralkyl or alkyl substituted by cycloalkyl, hydroxy, alkoxy, amino, alkylamino or dialkylamino; and $R_2$ represents hydrogen or $C_{1-4}$ alkyl group; or $R_1$ and $R_2$ together with the nitrogen atom to which they are attached form a 5 to 10 membered ring which may be saturated or may contain at least one double bond, may be unsubstituted or may be substituted by one or more $C_{1-3}$ alkyl groups, e.g. methyl, or a hydroxy group and/or may contain another heteroatom selected from oxygen or sulphur;

Alk represents a straight or branched alkylene chain of 1 to 3 carbon atoms;

Q represents a benzene ring in which incorporation into the rest of the molecule is through bonds at the 1- and 3- or 1- and 4-positions;

$R_5$ represents hydrogen or acyl;

n and m, which may be the same or different, are each 1 or 2;

$R_3$ represents hydrogen, alkyl, alkenyl, aralkyl, hydroxy $C_{2-6}$ alkyl, alkoxy $C_{2-6}$ alkyl or $C_{1-4}$ alkanoyloxy-$C_{2-6}$ alkyl; and $R_7$ represents hydrogen, alkyl, alkenyl, aralkyl, acyloxyalkyl, alkylthioalkyl, arylthioalkyl, aryloxyalkyl, aralkyloxyalkyl, or the group $(CH_2)_qR_6$ where q is zero, 1, 2, 3, 4, 5 or 6 and the alkylene chain $(CH_2)_q$ may be straight or branched, and $R_6$ is hydroxy, alkoxy, nitro, heteroaryl, tetrahydropyranyloxy or $CH_2NHC(=X)NHR_9$ where X represents NCN, $NSO_2$ Methyl, $NSO_2$ Phenyl or $CHNO_2$ and $R_9$ is alkyl;

or $R_6$ is the group $NR_{10}R_{11}$ where $R_{10}$ is hydrogen or alkyl; and $R_{11}$ is hydrogen, alkyl, alkenyl, aryl, aralkyl, or heteroaralkyl, or $R_{11}$ is the group $SO_2R_{12}$ where $R_{12}$ is alkyl or aryl or $R_{11}$ is the group $COR_{13}$ where $R_{13}$ is hydrogen, alkyl, aryl, aralkyl, alkoxy, halomethyl, heteroaryl, heteroaralkyl or the group $NHR_{14}$ where $R_{14}$ is hydrogen, alkyl, cycloalkyl, aryl or aralkyl; or $R_{10}$ and $R_{11}$ together represent the group $=CR_{15}R_{16}$ where $R_{15}$ represents aryl or heteroaryl and $R_{10}$ represents hydrogen or alkyl;

or $R_6$ is the group $SO_2R_{17}$ in which $R_{17}$ is hydroxy, alkyl, aryl or the group $NR_{18}R_{19}$ where $R_{18}$ and $R_{19}$, which may be the same or different, each represent hydrogen or alkyl;

or $R_6$ is the group $COR_{20}$ where $R_{20}$ is hydrogen, hydroxy, alkoxy, aryloxy, aralkyloxy, alkyl, aryl, aralkyl or the group $NR_{21}R_{22}$ where $R_{21}$ is hydrogen or alkyl optionally substituted by a hydroxy or alkoxy group; and $R_{22}$ is hydrogen, alkyl (optionally substituted by a hydroxy or alkoxy group), alkenyl, aryl, aralkyl or cycloalkyl, or $NR_{21}R_{22}$ forms a 5 to 8 membered ring which may contain another heteroatom, e.g. oxygen, or a double bond and/or may be substituted by hydroxy or one or two $C_{1-3}$ alkyl (e.g. methyl) groups; or $R_6$ is the group $CR_{23}=NR_{24}$ where $R_{23}$ is hydrogen, alkyl, aryl or aralkyl and $R_{24}$ is hydroxy, alkoxy, aralkyloxy or —NHC(=Y)NH$_2$ where Y is oxygen or sulphur;

or the groups $R_3$ and $R_7$ taken together represent $-(CH=CH)_2-$ or $-(CH_2)_4-$;

with the proviso that when the group $R_6$ contains a carbon atom through which it is linked to the alkylene group $(CH_2)_q$ then the total number of carbon atoms in the resulting chain is not greater than 6 (i.e. q is not greater than 5).

The term "alkyl" as a group or part of a group means that the group is straight or branched, and unless otherwise stated, has preferably 1 to 6 carbon atoms and in particular 1 to 4 carbon atoms, e.g. methyl or ethyl; and the terms "alkenyl" and "alkynyl" mean that the groups preferably contain 3 to 6 carbon atoms. The term "cycloalkyl" means that the group has 3 to 8 carbon atoms. The term "halomethyl" means a mono-, di- or trihalo substituted methyl group, e.g. trifluoromethyl. The term "aryl" as a group or part of a group preferably means phenyl or substituted phenyl, for example phenyl substituted with one or more $C_{1-3}$ alkyl or alkoxy groups or halogen atoms, e.g. fluorine. The term acyl or the acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term heteroaryl as a group or part of a group means a 5 or 6 membered monocyclic ring containing from 1 to 3 heteroatoms selected from oxygen, nitrogen and sulphur, e.g. thienyl, pyrrolyl, pyridyl, furyl or thiazolyl. The heteroaryl ring may be unsubstituted or substituted by $C_{1-3}$ alkyl, $C_{1-3}$ alkoxy, hydroxyalkyl, aminoalkyl, alkylaminoalkyl, dialkylaminoalkyl or halogen, for example, the heteroaryl ring may be thienyl or furyl substituted by $C_{1-3}$ alkyl, aminoalkyl, alkylaminoalkyl, dialkylaminoalkyl or hydroxyalkyl, pyrrolyl substituted by $C_{1-3}$ alkyl, pyridyl substituted by $C_{1-3}$ alkyl, $C_{1-3}$ alkoxy, halogen or hydroxyalkyl or thiazolyl substituted by $C_{1-3}$ alkyl or hydroxyalkyl. The alkyl portion of a heteroaralkyl group is a straight or branched $C_{1-4}$ alkyl chain, and the heteroaryl ring is linked to the alkyl portion through a carbon atom.

According to one aspect the invention provides compounds of formula (I) in which
$R_5$ represents hydrogen or a $C_{1-4}$ alkanoyl group;
$R_3$ represents hydrogen, alkyl, alkenyl, aralkyl, hydroxy $C_{2-6}$ alkyl or alkoxy $C_{2-6}$ alkyl;
$R_7$ is as defined in formula (I) except that $R_6$ does not represent tetrahydropyranyloxy; and
$R_1$, $R_2$, Alk, Q, n and m are as defined in formula (I).

Preferred compounds of formula (I) are those in which
$R_1$ represents $C_{1-8}$ alkyl (e.g. methyl, propyl, butyl or heptyl), $C_{1-4}$ alkyl substituted by a trifluoromethyl group (e.g. 2,2,2-trifluoroethyl), $C_{2-4}$ alkyl substituted by hydroxy or a di $C_{1-3}$ alkylamino group (e.g. 3-hydroxypropyl or dimethylaminoethyl), $C_{5-7}$ cycloalkyl (e.g. cyclohexyl), $C_{3-5}$ alkenyl (e.g. allyl), phenyl $C_{1-3}$ alkyl (e.g. benzyl), or a heteroaryl $C_{1-3}$ alkyl group where the heteroaryl ring contains one heteroatom (e.g. 2-furylmethyl);
$R_2$ represents hydrogen or methyl; or
$R_1R_2N$ represents a 5 to 7 membered ring optionally containing a double bond, an oxygen atom or an alkyl (e.g. methyl) substituent (e.g. piperidino, morpholino, 4-methylpiperidino, pyrrolidino, hexamethylenimino or tetrahydropyridino);
Alk represents methylene;
$R_3$ represents hydrogen, alkyl (e.g. methyl or ethyl), hydroxy $C_{2-4}$ alkyl (e.g. hydroxyethyl) or, $R_3$ and $R_7$ taken together represent $-CH=CH-_2$ or $-(CH_2)_4-$;
Q represents a benzene ring incorporated into the rest of the molecule through bonds at the 1- and 3-positions;
$R_5$ represents hydrogen or alkanoyl (e.g. acetyl);
n and m both represent 1 or one of n and m represents 2;
$R_7$ represents alkoxyalkyl, alkylthioalkyl, alkanoyloxyalkyl, benzyl, or $-CH=NOH$;
or $R_7$ represents the group $(CH_2)_qR_6$ where q is zero, 1, 2 or 3, and $R_6$ represents hydroxyl, $CH_2NHSO_2R_{12}$ (where $R_{12}$ is alkyl), $CH_2NHC(=X)NHCH_3$ (where $X=NCN$ or $CHNO_2$), $SO_2R_{17}$ (where $R_{17}$ is alkyl), or $R_6$ represents $COR_{20}$ where $R_{20}$ is hydroxyl or $NR_{21}R_{22}$ and $R_{21}$ and $R_{22}$ independently represent hydrogen or $C_{1-3}$ alkyl or $R_{21}$ and $R_{22}$ together with the nitrogen atom to which they are attached represent a pyrrolidino ring, or
$R_6$ represents the group $NR_{10}R_{11}$ where $R_{10}$ represents hydrogen and $R_{11}$ is hydrogen or $COR_{13}$, where $R_{13}$ represents hydrogen, alkyl, phenyl, benzyl, alkoxy, NH phenyl, or $R_{10}$ and $R_{11}$ together represent the group $=CHR_{15}$ where $R_{15}$ is phenyl or pyridyl. A further preferred class of compounds of formula (I) are those of formula (II)

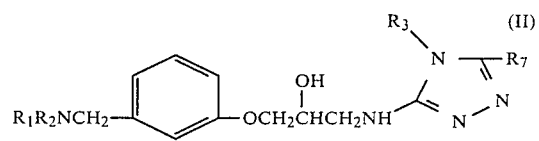

in which $R_1R_2N$ is dimethylamino, pyrrolidino, piperidino or hexamethylenimino, more preferably piperidino, $R_3$ is methyl and $R_7$ is amino or $R_3$ and $R_7$ together form the group $-(CH=CH)-_2$ or $(CH_2)_4$.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to the animal or human being are converted in the body into a compound of formula (I).

The compounds according to the invention, preferably in the form of a salt may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral or rectal administration. Oral administration is preferred.

For oral administration, the pharmaceutical compositions may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compound of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg to 1.5 g per day, preferably 5 to 500 mg per day dependent upon the condition of the patient.

It will be appreciated that in the methods of the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and/or $R_2$ in intermediates used to prepare compounds of formula (I) are hydrogen atoms and/or when $R_3$ in intermediates is an alkyl group bearing a hydroxy substituent and/or when $R_7$ in certain intermediates is an alkyl group bearing a hydroxy or primary or secondary amino substituent and/or when $R_5$ in intermediates is a hydrogen atom. Standard protection and deprotection procedures can be employed. For example an amino group may be protected by formation of a phthalimide which may subsequently be cleaved by treatment with a hydrazine e.g. hydrazine hydrate or a primary amine, for example methylamine; or by formation of a benzyl derivative which may subsequently be cleaved by hydrogenolysis in the presence of a catalyst e.g. palladium. The hydroxyl group $OR_5$ where $R_5$ is hydrogen may be protected, for example as an acyloxy group or as an ether group such as trialkylsilyl e.g. trimethylsilyl, aralkyl such as benzyl, benzhydryl or trityl, tetrahydropyranyl or alkoxymethyl, e.g. methoxymethyl ethers. Such protecting groups may be removed by conventional procedures of J F W McOmie. For example, benzyl and benzhydryl ether groups may be removed by catalytic hydrogenolysis with for example hydrogen and a palladium catalyst, and trityl, tetrahydropyranyl, alkoxymethyl and trialkylsilyl ether groups may be removed by acid hydrolysis.

In describing the processes which may be used for preparing the compounds of formula (I) or intermediates useful in the preparation thereof, any of $R_1$ to $R_3$, $R_5$ to $R_7$, $R_9$ to $R_{24}$, Alk, Q, n and m are as defined in formula (I) unless otherwise stated.

Compounds of formula (I) may be prepared by cyclisation of an appropriate intermediate. Thus, compounds of formula (I) in which $R_5$ represents hydrogen, other than compounds in which $R_7$ is acyloxyalkyl, alkoxy, nitro, $(CH_2)_qN=CR_{15}R_{16}$, $SO_2R_{17}$, $COR_{20}$ (where $R_{20}$ is hydrogen, aryl or aralkyl) or $CR_{23}=NR_{24}$, or compounds in which $R_3$ and $R_7$ together represent the group —CH=CH—$_2$ or —(CH$_2$)$_4$— may be prepared by cyclising a compound of formula (III)

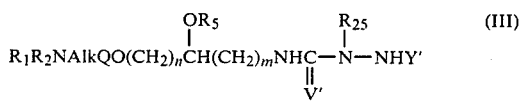

in which V' is $NR_3$, $R_{25}$ is hydrogen and Y' is

where Y" is sulphur, oxygen or NH.

In one embodiment of the cyclisation process; compounds of formula (I) may be prepared by cyclisation of a compound of formula (IV)

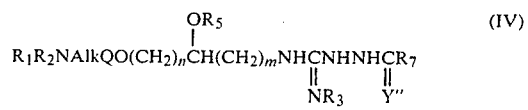

in which Y'" is oxygen.

The cyclisation may be carried out in the absence or presence of a solvent (e.g. dimethylformamide), at elevated temperatures (e.g. within the range 80°–150°) optionally in the presence of a base e.g. aqueous potassium hydroxide.

In a convenient embodiment of the cyclisation process the intermediate (IV) may be formed in situ by reacting an aminoguanidine of formula (V)

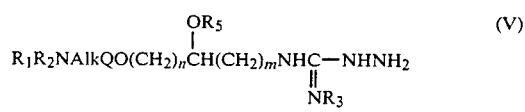

with cyanogen bromide or with an acid $R_7CO_2H$ or an activated derivative thereof, such as an acid halide (e.g. $R_7COCl$) or a trialkylorthoester (e.g. $R_7C(OEt)_3$). The reaction may be carried out by heating the acid and the aminoguanidine (V) under which conditions cyclisation of the intermediate (IV) takes place directly to give a compound of formula (I). In the case of an activated derivative an aprotic solvent, e.g. tetrahydrofuran may be used at temperatures from ambient to reflux. When using an acyl chloride as the activated derivative the reaction may also be carried out in the presence of a base, e.g. a tertiary amine such as pyridine, which may also be used as the solvent. The reaction with cyanogen bromide may be carried out with heating, optionally in the presence of a solvent such as an alkanol e.g. methanol.

The aminoguanidine (V) may be prepared, for example by reacting a diamine of formula (VI)

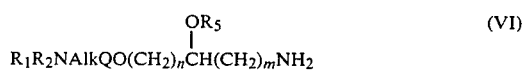

with a compound of formula (VII)

where L is a leaving group such as thioalkyl, e.g. thiomethyl.

Compounds of formula (I) in which $R_5$ is hydrogen and $R_7$ represents nitro or $R_3$ and $R_7$ together represent the group $+CH=CH+_2$, may be prepared by heating the diamine (VI) in which $R_5$ represents hydrogen with a compound of formula (VIII)

in which
$R_3'$ is the group $R_3$ or a group convertible thereto, and P is a leaving group such as halogen e.g. bromine.

The reaction may be carried out in the absence or presence of a solvent such as acetonitrile, water or an alcohol (e.g. ethanol) at for example 80°–150° C., and optionally in a sealed vessel.

In a particular embodiment of the process, triazoles in which $R_7$ is $NO_2$, i.e. q is zero and $R_6$ is $NO_2$, may be prepared by heating a diamine of formula (VI) with a triazole of formula (VIII) in which $R_7$ is $NO_2$.

Compounds of formula (VIII) in which P is bromine may be prepared from the corresponding triazole (VIII) in which P is hydrogen by treatment with bromine.

Compounds of formula (I) in which $R_5$ represents hydrogen and $R_7$ is the group $(CH_2)_qR_6$ where $R_6$ is $NR_{10}COR_{13}$, $NR_{10}SO_2R_{12}$, $CH_2NHC(=X)NHR_9$ or $N=CR_{15}R_{16}$ may be prepared by treating an aminoalkyltriazole of formula (IX)

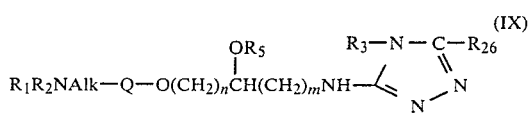

(IX)

in which $R_1$, $R_2$ and $R_3$ are as defined in formula (I) or are groups readily convertible thereto, and $R_{26}$ is the group $(CH_2)_qNHR_{10}$, the group $(CH_2)_{q+1}NH_2$ or the group $(CH_2)_qNH_2$, with a compound capable of replacing the hydrogen atom in the group $NHR_{10}$ by the group $COR_{13}$ or $SO_2R_{12}$ or a hydrogen atom in the group $NH_2$ of the group $(CH_2)_{q+1}NH_2$ by the group $C(=X)NHR_9$ or both hydrogen atoms in the group $NH_2$ of the group $(CH_2)_qNH_2$ by the group $=CR_{15}R_{16}$.

Thus for example the aminoalkyltriazole (IX) in which $R_{26}$ is the group $(CH_2)_q NHR_{10}$ may be reacted with an isocyanate $R_{14}'NCO$ in which $R_{14}'$ has any of the meanings defined for $R_{14}$ in formula (I) except hydrogen or represents an alkali metal atom such as potassium or sodium, or with an activated derivative of either a carboxylic acid $R_{13}COOH$ (in which $R_{13}$ is other than the group $NHR_{14}$) or a sulphonic acid $R_{12}SO_3H$ to give a compound of formula (I) in which $R_6$ is respectively the group $NR_{10}CONHR_{14}$, $NR_{10}COR_{13}$ (in which $R_{13}$ is other than $NHR_{14}$), or $NR_{10}SO_2R_{12}$.

Suitable activated derivatives include acid halides e.g. acid chlorides, alkylchloroformates, acid anhydrides including mixed anhydrides (e.g. acetic formic anhydride), esters such as alkyl esters, ortho esters and (1-alkyl-2-pyridinyl) esters.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride may be carried out in the absence or presence of solvent such as pyridine.

In the reaction with an isocyanate, compounds of formula (I) in which $R_{14}$ is other than hydrogen are conveniently prepared by carrying out the reaction in a solvent such as acetonitrile at temperatures from ambient to reflux. Compounds of formula (I) in which $R_{14}$ is hydrogen may be prepared by heating a salt e.g. hydrochloride of the aminotriazole (IX) with an aqueous solution of an appropriate cyanate, e.g. potassium cyanate.

As a further embodiment of this process an aminoalkyltriazole (IX) in which $R_{26}$ is the group $(CH_2)_{q+1}NH_2$ may be treated with a compound of formula $L'C(=X)NHR_9$ where $L'$ is a leaving group (e.g. methylthio) to give a compound of formula (I) in which $R_6$ is $CH_2NHC(=X)NHR_9$. The reactants may for example be mixed in an aqueous solution at room temperature.

In yet another embodiment of this process an aminoalkyltriazole (IX) in which $R_{26}$ is the group $(CH_2)_qNH_2$ is treated with an appropriate aromatic aldehyde, e.g. benzaldehyde, or a ketone $R_{15}R_{16}CO$ to give a product in which $R_6$ is $N=CR_{15}R_{16}$. The reaction may conveniently be carried out in the presence of a solvent e.g. benzene, preferably with heating e.g. at reflux.

Compounds of formula (I) in which $R_5$ is hydrogen and $R_7$ is the group $(CH_2)_qR_6$ in which $R_6$ is $COR_{20}$ (where $R_{20}$ is hydrogen, alkyl, aryl or aralkyl), or $SO_2R_{17}$ may be prepared by oxidation of the corresponding compound in which $R_7$ is the group $(CH_2)_qCHR_{20}OH$, $(CH_2)_qSR_{17}$ (where $R_{17}$ is other than hydroxy) or $(CH_2)_qSH$.

Thus aldehydes and ketones of formula (I) in which $R_5$ is hydrogen and $R_7$ is the group $(CH_2)_qCOR_{20}$ where $R_{20}$ is hydrogen, alkyl, aryl or aralkyl may be prepared by oxidising the corresponding hydroxyalkyl compound in which $R_7$ is $(CH_2)_qCHR_{20}OH$ using for example oxalyl chloride and dimethylsulphoxide, or activated manganese dioxide in a solvent such as dichloromethane.

Compounds of formula (I) in which $R_5$ is hydrogen and $R_7$ is the group $(CH_2)_qSO_2R_{17}$ may be prepared by oxidizing the corresponding compound in which $R_7$ is either $-(CH_2)_qSR_{17}$ (where $R_{17}$ is other than hydroxy) or $(CH_2)_qSH$ with for example peracetic acid. The reaction may be carried out in a solvent such as acetic acid, at room temperature.

The starting material in which $R_7$ is $(CH_2)_qSH$ where q is other than zero may be obtained by alkaline hydrolysis of the corresponding isothiourea, which may in turn be prepared by alkylating thiourea with an appropriate compound of formula (I) in which $R_6$ is a leaving group e.g. halo.

The thiol starting material in which $R_7$ is SH may be prepared by diazotisation of the corresponding aminotriazole followed by treatment with an alkali metal (e.g. potassium) salt of ethyl xanthate to give a xanthate in which $R_7$ is the group $-SC(=S)OEt$, which is subsequently hydrolysed (for example by heating with ethanolic potassium hydroxide) to give the starting thiol in which $R_7$ is the group SH.

The above oxidation process is particularly applicable to the preparation of compounds of formula (I) in which there is no unsaturation within the groups $R_1$ and $R_3$.

Compounds of formula (I) in which $R_5$ is hydrogen and $R_7$ is $(CH_2)_qCR_{23}=NR_{24}$ may be prepared by reacting the corresponding carbonyl compound i.e. a compound of formula (I) in which $R_7$ is $(CH_2)_qCOR_{23}$, with an appropriate reagent $H_2NR_{24}$ in a suitable solvent such as ethanol, optionally with heating.

Compounds of formula (I) in which $R_5$ is hydrogen, $R_7$ is $(CH_2)_qR_6$ where $R_6$ is $SO_2NR_{18}R_{19}$ or $CONR_{21}R_{22}$ may be prepared by reacting an activated derivative of the corresponding carboxylic acid or sulphonic acid, i.e. compounds of formula (I) in which $R_7$ is $(CH_2)_qR_6$ where $R_6$ is $CO_2H$ or $SO_3H$, with ammonia or an appropriate amine $HNR_{18}R_{19}$ or $HNR_{21}R_{22}$. Suitable activated derivatives include those referred to previously e.g. acid chlorides and esters.

Compounds of formula (I) in which $R_7$ is an acyloxyalkyl group and/or $R_5$ is acyl may be prepared by treating the corresponding compound of formula (I) in which $R_7$ is a hydroxyalkyl group and/or $R_5$ represents hydrogen with either an appropriate acid or an activated derivative thereof (e.g. an acid anhydride or acid chloride). The reaction may be carried out at room temperature optionally in the presence of a solvent (e.g. pyridine, tetrahydrofuran, acetone or dimethylformamide), and preferably in the presence of a base (e.g. pyridine, triethylamine or an alkali metal carbonate such as potassium carbonate).

Compounds of formula (I) in which $R_5$ is hydrogen and $R_3$ and $R_7$ together represent $-(CH_2)_4-$ may be prepared by reduction of the corresponding compound in which $R_3$ and $R_7$ together represent $-(CH=CH)_2$ using for example hydrogen and a metal catalyst (e.g. platinum) in a solvent such as ethanol.

Compounds of formula (I) in which Alk is $CH_2$ and $R_5$ is hydrogen may be prepared by treating an aldehyde of formula (X)

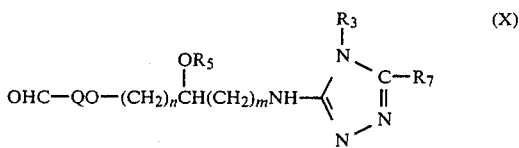

(X)

with an amine $R_1R_2NH$ in a solvent such as tetrahydrofuran or an alkanol, e.g. methanol, followed by reduction using for example a hydride reducing agent such as an alkali or alkaline earth metal borohydride e.g. sodium borohydride or lithium aluminium hydride, or hydrogen and a metal catalyst such as palladium or platinum. The reactions may be carried out at a temperature of 0° to 30° C.

The intermediates of formula (X) may be prepared from compounds of formula (XI)

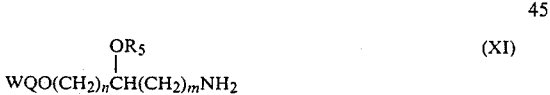

(XI)

in which W represents a protected aldehyde group, e.g. a cyclic acetal such as an ethylene acetal, by methods analogous to those described herein for preparing compounds of formula (I) from the amine of formula (VI).

Compounds of formula (I) in which $R_5$ is hydrogen and $R_6$ is tetrahydropyranyloxy may be prepared by reacting the corresponding hydroxyalkyltriazole of formula (I) with dihydropyran. The reaction may be carried out in a solvent, e.g. dichloromethane or dimethylformamide, at low temperature e.g. $-10°$ to $0°$ C., in the presence of a catalyst, e.g. paratoluenesulphonic acid.

In the above discussion of the processes available for the production of compounds according to the invention reference has been made to the primary amines of formula (VI) These amines are novel compounds and the invention includes such compounds. These intermediates may be made by a number of processes which are described below.

Diamines of formula (VI) in which $R_5$ is hydrogen and n is 1 may be prepared by reacting a compound of formula (XII)

$R_1R_2NAlkQOH$ (XII)

with an epoxide of formula (XIII)

(XIII)

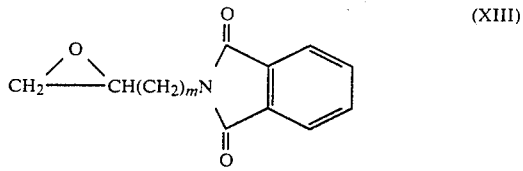

to produce a diamine of formula (XIV)

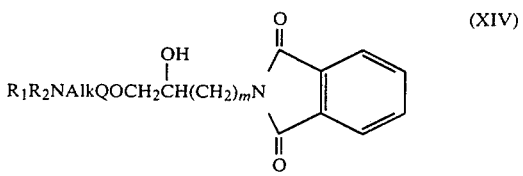

(XIV)

The reaction may be carried out in the absence or presence of a solvent such as dimethylformamide, preferably at elevated temperature, and optionally in the presence of a base, e.g. sodium hydride or potassium butoxide. The protecting group may be removed from the compound of formula (XIV) by reaction with a hydrazine, e.g. hydrazine hydrate, or a primary amine, e.g. methylamine.

Diamines of formula (VI) in which $R_5$ is hydrogen and m is 1 may be prepared by reacting an epoxide of formula (XV)

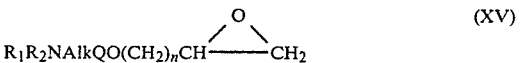

(XV)

with an azide, e.g. sodium azide to produce a compound of formula (XVI)

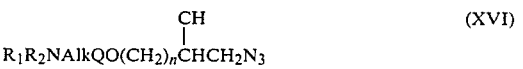

(XVI)

which may be reduced to produce a diamine of formula (VI) where m is 1. The reaction with the azide may be carried out in a suitable solvent, e.g. aqueous ethanol in the presence of ammonium chloride, preferably at reflux temperature. Reduction of the compound of formula (XVI) may be carried out for example, with lithium aluminium hydride in a suitable solvent, e.g. tetrahydrofuran, or catalytically using for example platinum oxide or palladium oxide as catalyst.

Diamines of formula (VI) in which $R_5$ is hdyrogen and m is 2 may be prepared by reacting the epoxide of formula (XV) with a cyanide, e.g. sodium cyanide, to produce a compound of formula (XVII)

(XVII)

which may be reduced to produce a compound of formula (VI) in which m is 2. The reaction with the cyanide may be carried out in a suitable solvent, e.g. aqueous ethanol preferably at reflux temperatures. Reduction of the compound of formula (XVII) may be carried out, for example with lithium aluminium hydride in a suitable solvent, e.g. tetrahydrofuran. Alternatively the epoxide of formula (XV) may be reacted with nitromethane to produce a compound of formula (XVIII)

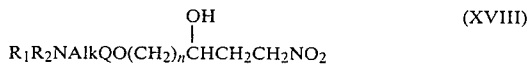

$$R_1R_2NAlkQO(CH_2)_n\overset{OH}{\underset{|}{C}}HCH_2CH_2NO_2 \quad (XVIII)$$

which may be reduced to produce a compound of formula (VI) in which m is 2. The reaction with nitromethane may be carried out in a suitable solvent, e.g. dimethylformamide, preferably in the presence of a base, e.g. sodium hydride. Reduction of the compound of formula (XVIII) may be carried out for example as described above for reduction of the compound of formula (XVII) or using hydrogen in the presence of a catalyst.

The intermediate epoxides of formula (XV) may be prepared by alkylation of an appropriate alkali metal phenolate, e.g. sodium phenolate with a halohydrin (XIX)

Hal $(CH_2)_nCH\overset{O}{\overset{/\quad\backslash}{\text{———}}}CH_2$ (XIX)

The intermediate epoxide of formula (XIII) may be prepared by alkylation of an alkali metal, phthalimide, e.g. potassium phthalimide with a halohydrin (XX)

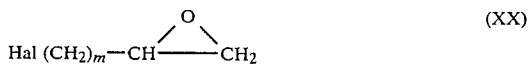

Hal $(CH_2)_m-CH\overset{O}{\overset{/\quad\backslash}{\text{———}}}CH_2$ (XX)

Where the product of any of the above processes is a free base and a salt is required, the salt may be formed in conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated but not limited by the following Examples.

In the following Examples and Preparations temperatures are in °C.

T.l.c. refers to thin layer chromatography and this and preparative chromatography were carried out on silica using, unless otherwise stated, one of the following solvent systems.

System A: Dichloromethane:ethanol:0.88 ammonia (50:8:1)
System B: Dichloromethane:ethanol:0.88 ammonia (100:8:1)
System C: Methanol:0.88 ammonia (200:1).

PREPARATION 1

2-[2-Hydroxy-3-[3-(1-piperidinylmethyl)phenoxy]-propyl]-1H-isoindole-1,3-(2H)dione A mixture of 2-(oxiranylmethyl)-1H-isoindole-1,3-(2H)-dione (9.10 g) and 3-(1-piperidinylmethyl)phenol (8.55 g) was heated at 130° C. under nitrogen for 10 minutes. The resulting mixture was dissolved in chloroform (100 ml), washed with 1N sodium hydroxide (2×25 ml), dried (MgSO4) and evaporated to give the title compound as a gum (17.65 g). T.l.c. system B, Rf 0.60.

PREPARATION 2

1-Amino-3-[3-(1-piperidinylmethyl)phenoxy]-2-propanol

A solution of 2-[2-hydroxy-3-[3-(1-piperidinylmethyl)phenoxy]propyl]-1H-isoindole-1,3-(2H) dione (17.6 g) and hydrazine hydrate (2.5 g) in ethanol (60 ml) was heated under reflux for 3 h. The resulting mixture was evaporated to a solid residue which was suspended in 1N hydrochloric acid (30 ml) and filtered. The filtrate was basified with an excess of potassium carbonate and extracted with isopropanol (3×40 ml). The isopropanol extracts were dried (Na2CO3) and evaporated to a gum which was chromatographed using System A. Crystallisation of the product from n-hexane:ether (20:1) gave the title compound as colourless grains (7.7 g) m.p. 74°–76.5°.

EXAMPLE 1

1-[3-(1-piperidinylmethyl)phenoxy]-3-[(1,2,4-triazolo[4,3,α]pyridin-3-yl)amino]-2-propanol A solution of 1-amino-3-[3-(1-piperidinylmethyl)-phenoxy]-2-propanol (1.6 g) and 3-bromo-1,2,4-triazolo[4,3-α]pyridine (1.2 g) in absolute ethanol (5 ml) was heated in an autoclave at 140° for 42 h. Aqueous 2M sodium carbonate (15 ml) was added to the reaction mixture and the solvent was evaporated to leave a dark brown solid. This solid was extracted with hot ethyl acetate. The ethyl acetate extract was cooled and partitioned with dilute hydrochloric acid (1M; 50 ml). The acidic aqueous layer was basified with excess aqueous sodium carbonate, washed with diethyl ether (50 ml) and then extracted with diethyl ether. The organic extracts were combined, dried (Na2SO4) and evaporated to leave a brown semi-solid gum. This gum was triturated with dry diethyl ether to precipitate a white solid (0.75 g) which was recrystallised from a mixture of ethyl acetate and methanol to give the title compound (0.15 g) as a white solid m.p. 160°–161°.

Analysis Found: C, 66.1; H, 6.9; N, 18.2; C21H27N5O2 requires: C, 66.1; H, 7.1; N, 18.4%.

EXAMPLE 2

1-[(5,6,7,8-Tetrahydro-1,2,4-triazolo[4,3-a]pyridin-3-yl)amino]-3-[3-(1-piperidinylmethyl)phenoxy]-2-propanol A solution of 1-[3-(1-piperidinylmethyl)phenoxy]-3-[(1,2,4-triazolo[4,3-a]pyridin-3-yl)amino]-2-propanol (252 mg) in absolute ethanol (25 ml) was hydrogenated over a 5% platinium on carbon catalyst (150 mg). After 8 h, additional catalyst (200 mg) was added and the mixture was hydrogenated for a further 8 h. The mixture was filtered through hyflo and the filtrate was evaporated to give a white solid which was recrystalised from ethyl acetate-methanol to give the title compound (182 mg) as white microcrystals, m.p. 141°–2°.

Found: C,65.1; H,8.1; N,18.7; C21H31N5O2 requires: C,65.4; H,8.1; N,18.2%.

EXAMPLES OF PHARMACEUTICAL COMPOSITIONS

| 1. Tablets | mg/tablet |
| --- | --- |
| Active ingredient | 5.0 to 25.0 |

| 1. Tablets | mg/tablet |
|---|---|
| Lactose | 131.5 to 111.5 |
| Pregelatinised maize starch | 7.5 |
| Sodium starch glycollate | 4.5 |
| Magnesium stearate | 1.5 |
| Compression weight | 150.0 |

The active ingredient is sieved through a 250 μm sieve and blended with the lactose and pregelatinised maize starch. This mix is granulated by the addition of water. The granules are dried, screened and blended with the sodium starch glycollate and magnesium stearate. The lubricated granules are compressed into tablets using 8.0 mm diameter punches.

| 2. Injections | % w/v |
|---|---|
| Active ingredient | 0.5 |
| Water for injection B.P. to | 100.0 |

Sodium chloride may be added to adjust the tonicity of the solution and the pH may be adjusted to that of maximum stability using dilute acid or alkali or by the addition of suitable buffer salts.

The solution is prepared, clarified and filled into appropriate sized ampoules sealed by fusion of the glass. The injection is sterilised by heating in an autoclave using one of the acceptable cycles. Alternatively the solution may be sterilised by filtration and filled in sterile ampoules under aseptic conditions.

The solution may be packed under as inert atmosphere of nitrogen or other suitable gas.

We claim:

1. A compound of formula (I)

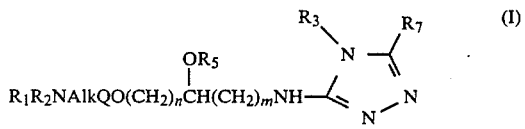

or a physiologically acceptable salt or hydrate thereof, in which $R_1$ represents hydrogen, $C_{1-14}$ alkyl, $C_{3-8}$ cycloalkyl, $C_{3-6}$ alkenyl, $C_{3-6}$ alkynyl, ar $C_{1-6}$ alkyl, trifluoro $C_{1-6}$ alkyl, heteroaralkyl, or $C_{1-6}$ alkyl substituted by $C_{3-8}$ cycloalkyl, hydroxy, $C_{1-6}$ alkoxy, amino, $C_{1-6}$ alkylamino or di $C_{1-6}$ alkylamino; and $R_2$ represents hydrogen or a $C_{1-4}$ alkyl group;

or $R_1$ and $R_2$ together with the nitrogen atom to which they are attached form piperidino, morpholino, 4-methyl piperidino, pyrrolidino, hexamethyleneimino or tetrahydropyridino;

Alk represents a straight or branched alkylene chain of 1 to 3 carbon atoms;

Q represents a benzene ring in which incorporation into the rest of the molecule is through bonds at the 1- and 3- or 1- and 4-positions;

$R_5$ represents hydrogen or acyl;

n and m, which may be the same or different, are each 1 or 2; and $R_3$ represents hydrogen, $C_{1-6}$ alkyl, $C_{3-6}$ alkenyl, ar $C_{1-6}$ alkyl, hydroxy $C_{2-6}$ alkyl, $C_{1-6}$ alkoxy $C_{2-6}$ alkyl or $C_{1-4}$ alkanoyloxy $C_{2-6}$ alkyl;

$R_7$ represents hydrogen, $C_{1-6}$ alkyl, $C_{3-6}$ alkenyl, ar $C_{1-6}$ alkyl, $C_{1-6}$ alkoxy $C_{1-6}$ alkyl, acyloxy $C_{1-6}$ alkyl, $C_{1-6}$ alkylthio $C_{1-6}$ alkyl, arylthio $C_{1-6}$ alkyl, aryloxy $C_{1-6}$ alkyl, ar $C_{1-6}$ alkyloxy $C_{1-6}$ alkyl, or the group $(CH_2)_qR_6$ where q is zero, 1, 2, 3, 4, 5, or 6 and the alkylene chain $(CH_2)_q$ may be straight or branched; and $R_6$ is hydroxy, $C_{1-6}$ alkoxy, nitro, heteroaryl, tetrahydropyranyloxy, or $CH_2NHC(=X)NHR_9$ where X represents NCN, $NSO_2$ Methyl, $NSO_2$ Phenyl or $CHNO_2$ and $R_9$ is $C_{1-6}$ alkyl;

or $R_6$ is the group $NR_{10}R_{11}$, where $R_{10}$ is hydrogen or $C_{1-6}$ alkyl; and $R_{11}$ is hydrogen, $C_{1-6}$ alkyl, $C_{3-6}$ alkenyl, aryl, ar $C_{1-6}$ alkyl, or heteroaralkyl, or $R_{11}$ is the group $SO_2R_{12}$ where $R_{12}$ is $C_{1-6}$ alkyl or aryl; or $R_{11}$ is the group $COR_{13}$ where $R_{13}$ is hydrogen, $C_{1-6}$ alkyl, aryl, ar $C_{1-6}$ alkyl, $C_{1-6}$ alkoxy, halomethyl, heteroaryl, heteroaralkyl or the group $NHR_{14}$ where $R_{14}$ is hydrogen, $C_{1-6}$ alkyl, $C_{3-8}$ cycloalkyl, aryl or ar $C_{1-6}$ alkyl; or $R_{10}$ and $R_{11}$ together represent the group $=CR_{15}R_{16}$ where $R_{15}$ represents aryl or heteroaryl and $R_{16}$ represents hydrogen or $C_{1-6}$ alkyl;

or $R_6$ is the group $SO_2R_{17}$ in which $R_{17}$ is hydroxy, $C_{1-6}$ alkyl, aryl or the group $NR_{18}R_{19}$ where $R_{18}$ and $R_{19}$, which may be the same or different, each represents hydrogen or $C_{1-6}$ alkyl;

or $R_6$ is the group $COR_{20}$ where $R_{20}$ is hydrogen, hydroxy, $C_{1-6}$ alkoxy, aryloxy, ar $C_{1-6}$ alkyloxy, $C_{1-6}$ alkyl, aryl, ar $C_{1-6}$ alkyl, or the group $NR_{21}R_{22}$ where $R_{21}$ is hydrogen or $C_{1-6}$ alkyl optionally substituted by a hydroxy or $C_{1-6}$ alkoxy group; and $R_{22}$ is hydrogen, $C_{1-6}$ alkyl (optionally substituted by a hydroxy or $C_{1-6}$ alkoxy group), $C_{3-6}$ alkenyl, aryl, ar $C_{1-6}$ alkyl or $C_{3-8}$ cycloalkyl, or $NR_{21}R_{22}$ forms a pyrrolidino ring which may be optionally substituted by hydroxy or one or two $C_{1-3}$ alkyl groups; or $R_6$ is the group $CR_{23}=NR_{24}$ where $R_{23}$ is hydrogen, $C_{1-6}$ alkyl, aryl or ar $C_{1-6}$ alkyl and $R_{24}$ is hydroxy, $C_{1-6}$ alkoxy, ar $C_{1-6}$ alkyloxy or $-NHC(=Y)NH_2$ where Y is oxygen or sulphur;

or $R_3$ and $R_7$ taken together represent $-(CH=CH)_2$ or $-(CH_2)_4-$;

with the proviso that when the group $R_6$ contains a carbon atom through which it is linked to the alkylene group $(CH_2)_q$ then the total number of carbon atoms in the resulting chain is not greater than 6, that is, q is not greater than 5; and wherein the term aryl as a group or part of a group means phenyl or phenyl substituted with one or more $C_{1-3}$ alkyl or alkoxy groups or halogen atoms; the term acyl or the acyl portion of an acyloxyalkyl group means an aroyl, aralkanoyl or $C_{1-6}$ alkanoyl group; the term heteroaryl as a group or part of a group means thienyl, pyrrolyl, pyridyl, furyl or thiazolyl, the heteroaryl ring may be unsubstituted or substituted by $C_{1-3}$ alkyl, $C_{1-3}$ alkoxy, hydroxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl or halogen, the alkyl portion of a heteroaralkyl group is a straight or barnched $C_{1-4}$ alkyl chain, and the heteroaryl ring is linked to the alkyl portion through a carbon atom.

2. A compound as claimed in claim 1 in which $R_1$ represents $C_{1-8}$ alkyl, $C_{1-4}$ alkyl substituted by a trifluoromethyl group, $C_{2-4}$ alkyl substituted by hydroxy or a di $C_{1-3}$ alkyl amino group, $C_{5-7}$ cycloalkyl, $C_{3-5}$ alkenyl, phenyl $C_{1-3}$ alkyl, or a heteroaryl $C_{1-3}$ alkyl group where the heteroaryl ring contains one heteroatom;

$R_2$ represents hydrogen or methyl; or $R_1R_2N$ as defined in claim 1;

Alk represents methylene;

$R_3$ represents hydrogen, $C_{1-6}$ alkyl, or hydroxy $C_{2-4}$ alkyl or $R_3$ and $R_7$, taken together, represent $-(CH=CH)_2-$ or $-(CH_2)_4-$;

Q represents a benzene ring incorporated into the rest of the molecule through bonds at the 1- and 3-positions;

$R_5$ represents hydrogen or $C_{1-6}$ alkanoyl;

n and m both represent 1, or one of n and m represents 2;

$R_7$ represents $C_{1-6}$ alkoxy $C_{1-6}$ alkyl, $C_{1-6}$ alkylthio $C_{1-6}$ alkyl, $C_{1-6}$ alkanoyloxy $C_{1-6}$ alkyl, benzyl, or $-CH=NOH$; or $R_7$ represents the group $(CH_2)_qR_6$ where q is zero, 1, 2, or 3, and $R_6$ represents hydroxyl, $CH_2NHSO_2R_{12}$ (where $R_{12}$ is $C_{1-6}$ alkyl), $CH_2NHC(=X)NHCH_3$ (where $X=NCN$ or $CHNO_2$), $SO_2R_{17}$ (where $R_{17}$ is $C_{1-6}$ alkyl), or $R_6$ represents $COR_{20}$ where $R_{20}$ is hydroxyl or $NR_{21}R_{22}$ and $R_{21}$ and $R_{22}$ independently represent hydrogen or $C_{1-3}$ alkyl or $R_{21}$ and $R_{22}$ together with the nitrogen atom to which they are attached represent a pyrrolidino ring; or $R_6$ represents the group $NR_{10}R_{11}$ where $R_{10}$ represents hydrogen and $R_{11}$ is hydrogen or $COR_{13}$, where $R_{13}$ represents hydrogen, $C_{1-6}$ alkyl, phenyl, benzyl, $C_{1-6}$ alkoxy, NH phenyl, or $R_{10}$ and $R_{11}$ together represent the group $=CH_{15}$ where $R_{15}$ is phenyl or pyridyl.

3. A compound as claimed in claim 1 in which
$R_5$ represents hydrogen or a $C_{1-4}$ alkanoyl group;

$R_3$ represents hydrogen, $C_{1-6}$ alkyl, $C_{3-6}$ alkenyl, ar $C_{1-6}$ alkyl, where aryl is as defined in claim 6, hydroxy $C_{2-6}$ alkyl or $C_{1-6}$ alkoxy $C_{2-6}$ alkyl;

$R_7$ is as defined in claim 1, except that $R_6$ does not represent tetrahydropyrangloxy; and $R_1$, $R_2$, Alk, Q, n and m are as defined in claim 1.

4. A compound as claimed in claim 1 of formula (II)

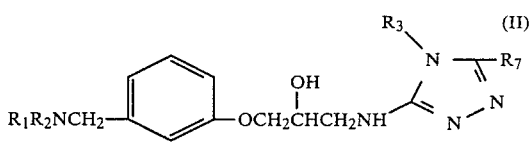

in which $R_1R_2N$ is dimethylamino, pyrrolidino, piperidino or hexamethylenimino, $R_3$ is methyl and $R_7$ is amino or $R_3$ and $R_7$ together form the group $-(CH=CH)_2-$ or $(CH_2)_4$.

5. A pharmaceutical composition for the treatment of conditions mediated through histamine $H_2$-receptors which comprises an effective amount to relieve said condition of a compound as claimed in claim 1 together with at least one inert pharmaceutically acceptable carrier or diluent.

6. A method of treating a condition mediated through histamine $H_2$-receptors which comprises administering to a patient an effective amount of a compound as claimed in claim 1 to relieve said condition.

* * * * *